US011085009B2

(12) United States Patent
Brain et al.

(10) Patent No.: US 11,085,009 B2
(45) Date of Patent: *Aug. 10, 2021

(54) ENHANCED DEPOSITION OF ETHYL VANILLIN OR VANILLIN WITH FRIABLE MICROCAPSULES

(71) Applicant: International Flavors & Fragrances Inc., New York, NY (US)

(72) Inventors: Joseph Brain, Colts Neck, NJ (US); Robert Muir, Leonardo, NJ (US); Tamara Wynn Hopkins, Jersey City, NJ (US)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/571,692

(22) Filed: Sep. 16, 2019

(65) Prior Publication Data

US 2020/0040284 A1 Feb. 6, 2020

Related U.S. Application Data

(63) Continuation-in-part of application No. 14/435,395, filed as application No. PCT/US2013/064250 on Oct. 10, 2013, now Pat. No. 10,415,002.

(60) Provisional application No. 61/713,016, filed on Oct. 12, 2012.

(51) Int. Cl.
*C11D 3/50* (2006.01)
*C11B 9/00* (2006.01)

(52) U.S. Cl.
CPC ............ *C11D 3/505* (2013.01); *C11B 9/0061* (2013.01)

(58) Field of Classification Search
CPC ......... C11B 9/0061; A61K 8/11; A61K 8/347; A61K 8/84; A61K 8/37; A61K 2800/413; A61Q 5/02; A61Q 19/10; A61Q 15/00; A61Q 17/04; C11D 3/2072; C11D 3/505; C11D 3/001; D06M 13/005; D06M 23/12; B01J 13/20
See application file for complete search history.

(56) References Cited

U.S. PATENT DOCUMENTS

| 4,234,627 | A * | 11/1980 | Schilling | C11D 3/0015 510/101 |
| 4,464,271 | A * | 8/1984 | Munteanu | A61K 8/11 510/101 |
| 6,045,835 | A | 4/2000 | Soper et al. | |
| 7,491,687 | B2 * | 2/2009 | Popplewell | A61K 8/11 424/401 |
| 7,538,079 | B2 | 5/2009 | Warr et al. | |
| 9,464,263 | B2 * | 10/2016 | Aussant | C11D 17/0039 |
| 10,415,002 | B2 * | 9/2019 | Brain | C11D 3/505 |
| 2005/0112152 | A1 | 5/2005 | Popplewell et al. | |
| 2010/0168251 | A1 | 7/2010 | Warr et al. | |
| 2011/0110997 | A1 | 5/2011 | Cunningham et al. | |
| 2013/0164355 | A1 * | 6/2013 | Aussant | C11D 3/0015 424/401 |
| 2015/0017214 | A1 * | 1/2015 | Warr | A61Q 5/12 424/401 |
| 2015/0267144 | A1 * | 9/2015 | Brain | C11D 3/505 510/102 |
| 2015/0291910 | A1 * | 10/2015 | Popplewell | A61K 8/92 512/4 |
| 2016/0089464 | A1 * | 3/2016 | Frankenbach | A61K 8/31 424/76.1 |
| 2016/0175214 | A1 * | 6/2016 | Scavone | A61K 8/375 424/401 |
| 2016/0177222 | A1 * | 6/2016 | Bianchetti | A61Q 19/10 424/65 |
| 2020/0040284 | A1 * | 2/2020 | Brain | C11B 9/0061 |

FOREIGN PATENT DOCUMENTS

| CN | 1689693 A | 11/2005 | |
| EP | 0841391 A1 | 5/1998 | |
| EP | 1533364 A2 * | 5/2005 | ............... C11D 3/37 |
| EP | 1533364 A2 | 5/2005 | |
| WO | 2011158962 A2 | 12/2011 | |
| WO | 2014059087 A2 | 4/2014 | |
| WO | WO-2016124746 A1 * | 8/2016 | ........... C11B 9/0061 |

OTHER PUBLICATIONS

Chinese First Office Action dated Jan. 23, 2017 for Application No. CN 201380053437.5.
Extended European Search Report dated May 3, 2016 for Application No. 13845516.7.
International Preliminary Report on Patentability in PCT/US2013/064250 dated Jun. 16, 2015.
International Search Report and Written Opinion in PCT/US2013/064250 dated Dec. 9, 2013.
Office Communication dated Jan. 14, 2016 from U.S. Appl. No. 14/435,395, filed Apr. 13, 2015.
Office Communication dated Jul. 21, 2016 from U.S. Appl. No. 14/435,395, filed Apr. 13, 2015.
Office Communication dated Nov. 2, 2017 from U.S. Appl. No. 14/435,395, filed Apr. 13, 2015.
Office Communication dated Aug. 9, 2018 from U.S. Appl. No. 14/435,395, filed Apr. 13, 2015.

* cited by examiner

*Primary Examiner* — Vasudevan S Jagannathan
*Assistant Examiner* — Preeti Kumar
(74) *Attorney, Agent, or Firm* — Licata & Tyrrell P.C.

(57) ABSTRACT

The present invention is an ethyl vanillin and/or vanillin friable shell-core microcapsule composition prepared by combining ethyl vanillin or vanillin with preformed friable shell-core microcapsules for a time sufficient for the ethyl vanillin or vanillin and microencapsulates to interact. Wash off consumer products and a method for depositing ethyl vanillin or vanillin on a surface are also provided.

12 Claims, No Drawings

ENHANCED DEPOSITION OF ETHYL VANILLIN OR VANILLIN WITH FRIABLE MICROCAPSULES

CROSS-REFERENCE TO RELATED APPLICATIONS

This application claims priority to U.S. patent application Ser. No. 14/435,395, filed on Apr. 13, 2015, which is a national phase entry under 35 USC 371 for International Application No. PCT/US2013/064250 filed Oct. 10, 2013. The international application claims priority to U.S. Patent Application Ser. No. 61/713,016 filed on Oct. 12, 2012. The contents of the applications are incorporated herein by reference in their entirety.

BACKGROUND OF THE INVENTION

Encapsulation of fragrance and flavor materials provides advantages to the fragrance/flavor product including the protection of the fragrance/flavor in the capsule core by a shell until the fragrance/flavor is intended to be delivered. In particular, capsules are often designed to deliver their contents at a desired time by the capsule shell being compromised at the desired time.

The capsule shell can be compromised by various factors such as temperature so that the contents are delivered when the capsule begins to melt. Alternatively the capsules can be compromised by physical forces, such as crushing, or other methods that compromise the integrity of the capsule. Additionally, the capsule contents may be delivered via diffusion through the capsule wall during a desired time interval.

SUMMARY OF THE INVENTION

The present invention is a composition composed of friable shell-core microcapsules and ethyl vanillin and/or vanillin, wherein said composition is formed by combining preformed friable shell-core microcapsules with vanillin and/or ethyl vanillin for a time sufficient for the friable shell-core microcapsule and fragrance to interact. A method for preparing the friable shell-core microcapsule composition is also provided. In some embodiments, the friable shell-core microcapsule is composed of urea-formaldehyde, melamine-formaldehyde, phenol-formaldehyde, or amido-aldehyde. In other embodiments, the friable shell-core microcapsule also includes a surfactant or solvent, e.g., a triglyceride ester of a mixture of caprylic acid and capric acid. A wash off consumer product and method for depositing ethyl vanillin on a surface using the wash off consumer product are also provided.

Also within the scope of this invention is a fabric conditioner composition prepared by a method comprising the steps of: (a) mixing ethyl vanillin or vanillin with a slurry containing preformed friable shell-core microcapsules, each of which has a core and a shell; (b) aging the mixture of step (a) to allow ethyl vanillin or vanillin to interact with the preformed friable shell-core microcapsules; and (c) combining the aged mixture of step (b) with a fabric conditioner base (e.g., at a level of 0.05% to 5% by weight of the combined mixture), wherein the preformed friable shell-core microcapsules each have a diameter of 0.5 microns to 100 microns, and the ethyl vanillin or vanillin is added at a concentration of 0.05% to 20% by weight of the mixture of step (a). Preferred friable shell-core microcapsules have a shell formed of urea-formaldehyde, melamine-formaldehyde, phenol-formaldehyde, or amido-aldehyde and the core contains a solvent.

In some embodiments, the fabric conditioner composition has a first fragrance in the slurry, a second fragrance in the core, or both. Preferably, at least one of the first and second fragrances is a high performing fragrance such as those described in WO2018071897.

The fabric conditioner composition can be either a rinse added composition (i.e., added during rinse within a washing cycle) or a dryer sheet.

The fabric conditioner composition contains a fabric conditioner base, which is optionally melted at an elevated temperature (e.g., 50-90° C.) before being combined with the aged mixture of step (b).

DETAILED DESCRIPTION OF THE INVENTION

Ethyl vanillin (Clog P of 2.84) and vanillin are relatively water soluble fragrance ingredients. Ethyl vanillin and vanillin are not typically included at large quantities in a neat oil of a fabric conditioner because they will not deposit on the cloth and will be washed away. Moreover, ethyl vanillin and vanillin are not conventionally encapsulated in microcapsules by loading a preformed microcapsule because their water soluble nature causes these fragrances to leak out of the microcapsule. However, it has now been found that the incorporation of ethyl vanillin or vanillin in a melamine formaldehyde slurry produces a microcapsule that allows ethyl vanillin or vanillin to deposit on cloth, via a wash off product, to provide the vanilla sweet note at the dry stage of fabric. Therefore, this invention is a method of preparing an ethyl vanillin or vanillin friable shell-core microcapsule composition by combining ethyl vanillin and/or vanillin with preformed friable shell-core microcapsules and aging the mixture for a time sufficient for the ethyl vanillin/vanillin and microcapsules to interact. The invention is also a wash off consumer product containing the ethyl vanillin/vanillin friable shell-core microcapsule composition and a method for depositing ethyl vanillin and/or vanillin onto a surface via said wash off consumer product.

In accordance with the preparation of microcapsules of this invention, ethyl vanillin and/or vanillin is used as a neat fragrance at about 5% to about 30% by weight of the neat fragrance. More preferably, the ethyl vanillin and/or vanillin is used at about 10% to about 20% by weight of a neat fragrance. To achieve the desired concentration of ethyl vanillin and/or vanillin, the ethyl vanillin and/or vanillin can be provided in a suitable solvent such as dipropylene glycol (DPG).

To produce the composition of the invention, ethyl vanillin and/or vanillin is combined with the friable shell-core microcapsule slurry or formulation and aged, e.g., for at least 24 hours, to form ethyl vanillin and/or vanillin friable shell-core microcapsules. The ethyl vanillin and/or vanillin can be present at a final concentration of between 0.05% to 20% by weight of the microcapsule composition. More preferably, the ethyl vanillin and/or vanillin is present at a final concentration of about 0.05%, 0.1%, 0.5%, 1.0%, 1.5%, 2.0%, 3.0%, 4.0%, 5.0%, or up to 20% by weight of the microcapsule composition.

In some embodiments, combinations of different active ingredients may be combined into one system. Specifically, two separate fragrances may be combined in the same system to provide a dual fragrance effect in the final product. For example, in addition to ethyl vanillin or vanillin, a second fragrance can be encapsulated in the core of the microcapsule and/or provided in the friable shell-core microcapsule slurry. Other suitable fragrances that can be combined with the ethyl vanillin or vanillin include, but are not limited to, coumarin, amyl salicylate, benzyl benzoate, benzyl salicylate, galaxolide, methyl jasmonate, and isopropyl myristate.

As indicate, the microcapsules of this invention are friable. Friability refers to the propensity of the capsules to rupture or break open when subjected to direct external pressures or shear forces. For the purposes of this invention, a capsule is "friable" if, while attached to a treated surface (e.g., a fabric), the microcapsule can be ruptured by the forces encountered when the microcapsule-containing surface is manipulated, e.g., by being worn, handled or ironed thereby releasing the contents of the microcapsule.

The microcapsules of the invention can be prepared using a range of conventional methods known to those skilled in the art for making friable shell-core microcapsules, such as interfacial polymerization and polycondensation. See, e.g., U.S. Pat. Nos. 3,516,941, 4,520,142, 4,528,226, 4,681,806, 4,145,184; GB 2,073,132; WO 99/17871; and *Microencapsulation: Methods and Industrial Applications*, Edited by Benita and Simon (Marcel Dekker, Inc. 1996). It is recognized that many variations with regard to materials and process steps are possible, however, non-limiting examples of friable shell materials suitable for making a friable shell of the microcapsule of this invention include urea-formaldehyde, melamine-formaldehyde, phenol-formaldehyde, amido-aldehyde, gelatin, gelatin/gum arabic blend, polyurethane, polyamides, or combinations thereof. In particular embodiments, the friable shell material comprises melamine cross-linked with formaldehyde.

Melamine formaldehyde microcapsules can be prepared from cationic melamine-formaldehyde condensates as disclosed in U.S. Pat. No. 5,401,577; melamine formaldehyde microencapsulation as disclosed in U.S. Pat. No. 3,074,845; melamine formaldehyde microcapsules in U.S. Pat. No. 4,525,520; cross-linked oil-soluble melamine formaldehyde precondensate in U.S. Pat. No. 5,011,634; capsule wall material formed from a complex of cationic and anionic melamine formaldehyde precondensates that are then cross linked as disclosed in U.S. Pat. No. 5,013,473; melamine-formaldehyde chemistry as disclosed in GB 2 062 570 A; and capsules cross-linked with melamine-formaldehyde as disclosed in U.S. Pat. No. 4,001,140. The formaldehyde to melamine molar ratio of the microcapsules of this invention can be from 2.30:5.50 or as low as 0.20:0.49 (Long, et al. (2009) *J. Mater. Chem.* 19:6882-6887).

Methods for preparing capsules with urea formaldehyde, urea aldehyde, or amido-aldehyde are disclosed in, e.g., U.S. Pat. No. 5,204,185, EP 0 443 428 A2, U.S. Pat. No. 3,516,941 and EP 0 158 449 A1.

The average outside diameter of the resulting microcapsule is in the range of from about 0.01 microns to about 1000 microns; preferably from about 0.05 microns to about 100 microns and more preferably from about 2.0 microns to about 20 microns. The average wall thickness of the resulting microcapsule is in the range of from about 0.001 microns to about 100 microns; preferably from about 0.005 microns to about 10 microns and more preferably from about 0.2 microns to about 2.0 microns.

In addition to fragrances, the friable shell-core microcapsules can be combined with an emulsifier or surfactant before or after combining the same with ethyl vanillin or vanillin. Examples of suitable emulsifiers or surfactants include, but are not limited to, lecithins, sucrose esters, proteins, gums, soap-bark extract, saponins, and the like.

Moreover, a variety of solvents can be used in combination with the friable shell-core microcapsule composition of this invention. The solvent used in combination with friable shell-core microcapsule composition is preferably a mono-, di- or tri-$C_4$-$C_{26}$ saturated or unsaturated fatty acid glyceride, diethyl phthalate, dibutyl phthalate, diisodecyl adipate, a liquid polydimethyl siloxane, a liquid polydimethylcyclosiloxane, the methyl ester of soya fatty acid, a mixture of soya fatty acid methyl ester and isopropyl myristate with the weight ratio of soya fatty acid:isopropyl myristate being from 2:1 to 20:1 and a mineral oil compatible with the ethyl vanillin. More preferably, the solvent is a tri-$C_4$-$C_{26}$ saturated or unsaturated fatty acid glyceride. Most preferably, the solvent is the triglyceride ester of a mixture of caprylic acid and capric acid, commercially available as NEOBEE M-5 (Stepan Chemical Company). The C $\log_{10}P$ of the solvent is greater than 3.3, where P is the n-octanol/water partition coefficient of the hydrophobic solvent; preferably greater than about 8 and most preferably greater than about 10. In some embodiments, the microcapsules are suspended in a solvent disclosed herein. In other embodiments, the solvent is in the core of the microcapsule. In further embodiments, the solvent is in the core and used to suspend the microcapsules.

Once combined and mixed, the ethyl vanillin/vanillin friable shell-core microcapsule composition can then be stored for 24 hours or more and/or incorporated into a consumer wash off product. The microcapsules are incorporated into the consumer wash off product at a level of between 0.05% to 5% by weight of the wash off product. More preferably, microcapsules are incorporated into the consumer wash off product at a level of about 0.05%, 0.1%, 0.5%, 1.0%, 1.5%, 2.0%, 3.0%, 4.0%, or 5.0% by weight of the wash off product.

Desirably, once the consumer wash off product is applied to a surface, the ethyl vanillin and/or vanillin fragrance is released. Indeed, in accordance with this invention, when ethyl vanillin and/or vanillin is pre-mixed with a slurry of friable shell-core microcapsules, an interaction with the friable shell material is observed that allows ethyl vanillin and/or vanillin to deposit on a surface, e.g., cloth, via a wash off product thereby providing the vanilla sweet note at the damp, dry and ironing stage.

The ability of the capsules of the invention to release ethyl vanillin and/or vanillin can be analyzed by conventional techniques. For example, when the wash off consumer product is a fabric conditioner, the fabric conditioner can be used to wash a load of towels in either a top or front loading washing machine. The towels are then evaluated by expert panelists to determine whether the pre-rub of the towel contains more ethyl vanillin/vanillin than if the ethyl vanillin/vanillin was used as a neat fragrance in the fabric conditioner. An enhanced sweet character is proof that the ethyl vanillin/vanillin is interacting with the microcapsule in a way that increases the performance of the ingredient compared to ethyl vanillin/vanillin added as a neat fragrance to a fabric conditioner.

Similarly, the ability of the microcapsule to increase the performance of ethyl vanillin/vanillin can be assessed by deposition of the ethyl vanillin/vanillin friable shell-core microcapsule composition on a fabric, e.g., in a fabric conditioner, and ironing the fabric. If an increased bloom in fragrance is observed compared to neat fragrance, the ethyl vanillin/vanillin friable shell-core microcapsule composition is considered to increase the performance (e.g., increase deposition) of the fragrance ingredient in a wash off product.

According to this invention, the ethyl vanillin/vanillin microcapsule compositions can be applied topically to a variety of surfaces to deliver the active ingredients of the microcapsule. For example, the microcapsule can be applied to substrates such as cloth, hair, and skin during washing and rinsing processes. Accordingly, the microcapsules of this invention are particularly suitable for wash off product. As used in the context of this invention, wash off products are understood to be those products that are applied for a given period of time and then are removed. Products suitable for this invention are common in areas such as laundry products, and include detergents, fabric conditioners, spray on starch, spray on sizing, fabric fresheners, and the like; as well as personal care products which include shampoos, hair rinses, body washes, soaps, anti-perspirants, deodorants, sunscreens, insect repellents and the like. These products employ surfactant and emulsifying systems that are well known. For example, fabric conditioner systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, 4,767,547, 4,424,134. Liquid laundry detergents which can use the present invention include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. Shampoo and conditioners that can employ the present invention include U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090 and 4,705,681.

In some embodiments, the water in the microcapsule composition may be removed to provide a final product in powder form. In this respect, spray dry carriers can be used in the instant compositions. Spray dry carriers include, but are not limited to, carbohydrates such as chemically modified starches and/or hydrolyzed starches, gums such as gum arabic, proteins such as whey protein, cellulose derivatives, clays, synthetic water-soluble polymers and/or copolymers such as polyvinyl pyrrolidone, polyvinyl alcohol. The spray dry carriers may be present in an amount from about 1% to about 50%, more preferably from about 5% to about 20%.

Optionally, a free flow agent (anti-caking agent) can be used. Free flow agents include silicas which may be hydrophobic (i.e., silanol surface treated with halogen silanes, alkoxysilanes, silazanes, siloxanes, etc. such as SIPERNAT D17, AEROSIL R972 and R974 (available from Degussa), etc.) and/or hydrophilic such as AEROSIL 200, SIPERNAT 22S, SIPERNAT 50S, (available from Degussa), SYLOID 244 (available from Grace Davison). The free flow agents may be present from about 0.01% to about 10%, more preferable from 0.5% to about 5%.

Further suitable humectants and viscosity control/suspending agents can also be included and are disclosed in U.S. Pat. Nos. 4,428,869, 4,464,271, 4,446,032, and 6,930,078. Details of hydrophobic silicas as a functional delivery vehicle of active materials other than a free flow/anti-caking agent are disclosed in U.S. Pat. Nos. 5,500,223 and 6,608,017.

In other embodiments of the present invention, the final composition or product may be in the form of an oil, a gel, a solid stick, a lotion, a cream, a milk, an aerosol, a spray, a powder, a foam, a shampoo, a hair conditioner, a lacquer or a make-up.

In embodiments pertaining to spray-dried microcapsule compositions, such compositions can include products such as powder laundry detergent, fabric conditioner dryer sheets, household cleaning dry wipes, powder dish detergent, floor cleaning cloths, or any dry form of personal care products (e.g., shampoo powder, conditioner, personal wash, deodorant powder, foot powder, soap powder, baby powder), etc. Because of high fragrance and/or active agent concentration in the spray-dried products of the present invention, characteristics of the aforementioned consumer dry products will not be adversely affected by a small dosage of the spray-dried products.

The invention is described in greater detail by the following non-limiting examples.

Example 1: Sweet Note of Ethyl Vanillin Plus Pre-Formed Capsule Premix

Ethyl vanillin/pre-formed microcapsule premix was prepared by mixing a neat fragrance oil that contained ethyl vanillin and coumarin fragrance ingredients, surfactant and an aqueous slurry of pre-formed capsules for a time sufficient to create a stable emulsion. The resulting premix was tested to ensure performance. For this test, the premix was incorporated into a fabric conditioner, a cloth was washed with the fabric conditioner, and the cloth was evaluated at the dry stage (pre- and post-rub). The results were compared to a reference sample where the neat fragrance and microcapsules were individually dosed directly into the fabric conditioner base.

During one of these tests, a unique ethyl vanillin/microcapsule interaction was noted on the dry cloth. For certain microcapsules there was a distinct difference in odor of the washed towels treated with the reference sample (neat fragrance and microcapsule added separately) compared to the premix prepared fabric conditioner sample. The washed towels treated with the premix prepared sample contained a strong sweet note at the pre-rub and post-rub stage.

Tests were run based on taking out specific ingredients to determine which ingredient was causing this strong sweet note. Ethyl vanillin and coumarin were separately excluded from the microcapsule premix. Towels were washed with the microcapsule premix containing or lacking ethyl vanillin or coumarin. The sweet note on pre- and post-rub was not present when the ethyl vanillin was absent from the formulation. The microcapsule premix containing coumarin did not provide the same result. Therefore, it was concluded that the ethyl vanillin caused this phenomena.

Example 2: Performance of Ethyl Vanillin Plus Microcapsule Premix in a Dilute Fabric Conditioner A 20% solution of ethyl vanillin was prepared by adding 20 grams of ethyl vanillin to DPG. A neat oil/microcapsule premix was prepared by adding ethyl vanillin (final concentration of 0.1% or 1%) and surfactant to an aqueous slurry of pre-formed microcapsules containing neobee oil, i.e., essentially unfragranced capsules. The combination was sufficiently mixed to create an emulsion and allowed to age for a minimum of 24 hours. The microcapsule pre-mix containing 0.1% or 1% ethyl vanillin were combined with a dilute fabric conditioner at a final amount of 1.5%. Reference samples were also prepared. These included the addition of unfragranced microcapsules to a dilute fabric conditioner base at a final amount of 1.43%; and addition of unfragranced microcapsules+0.07% ethyl vanillin added separately to a dilute fabric conditioner at a final amount of 1.5%. All preparations were aged for 3 hours, and evaluated for fragrance intensity. This analysis indicated that the way in which ethyl vanillin was added to the fabric conditioner base) made a significant difference in fragrance intensity. When creating a pre-mix of ethyl vanillin and microcapsules and aging the mixture overnight, there was a stronger sweet vanilla note compared to samples where the ethyl vanillin and capsules were added separately and directly to the base.

Example 3: Performance Comparison of Ethyl Vanillin/Microcapsule Premix vs. NEOBEE Core Capsules A Microcapsule premix was prepared by combining 5.280 g of 20% ethyl vanillin (in DPG), 0.285 g NEOBEE, 0.143 g TWEEN 20, and 94.292 g of an aqueous slurry of performed microcapsules with NEOBEE oil in the core. A reference sample was also prepared, which included unfragranced microcapsules with NEOBEE oil. Each mixture was aged for 24 hours and added to a dilute fabric conditioner base at 1.5% or 3.0% by weight. The resulting fabric conditioners were used to wash and evaluate towels for fragrance intensity at all wash stages. The results of this analysis are presented in Table 1.

TABLE 1

| | | Strength | | | | | |
|---|---|---|---|---|---|---|---|
| | | Heat Dry | | Line Dry | | | |
| % In Base | ID | Pre-Rub | Post-Rub | Pre-Rub | Post-Rub | Damp | P.O.P | Comment |
| 1.5 | Reference Sample | 1.4 | 1.5 | 1.1 | 1.7 | 1.6 | 1.9 | Base |
| 3.0 | Reference Sample | 1.3 | 1.4 | 1.2 | 1.9 | 1.7 | 2 | Base |
| 1.5 | Fragrance Microcapsules | 3.2 | 3.9 | 2.4 | 4 | 3.1 | 2.9 | Vanilla Sweet, Very Slight Base |
| 3.0 | Fragrance Microcapsules | 3.6 | 4.1 | 2.4 | 3.4 | 3.6 | 3.3 | Vanilla Sweet |

This analysis indicated that the towels washed with fabric conditioner containing the ethyl vanillin/microcapsule premix had a very good strength of fragrance at pre- and post-rub. NEOBEE microcapsules did not provide a post-rub benefit on their own, but when ethyl vanillin was premixed with the pre-formed microcapsules, a burst effect was noticed after rubbing the dry towels washed with this fabric conditioner.

Example 4: Bloom of Samples after Ironing

Four samples were prepared in fabric conditioner: microcapsules (1.43%% by weight) containing NEOBEE in the core; ethyl vanillin solution only (0.07% by weight); a premix of ethyl vanillin plus pre-formed microcapsule with NEOBEE in the core (1.5% by weight); and microcapsules (1.43% by weight)+ethyl vanillin solution (0.07% by weight) added separately to the fabric conditioner. Each sample was used to wash and evaluate towels. Each sample was evaluated at damp, heat dry (pre- and post-rub), and line dry (pre- and post-rub) using a scale from 0-5, with 0 being the lowest and 5 being the highest on strength intensity. The results of this analysis are presented in Table 2.

TABLE 2

| | Intensity |
|---|---|
| Damp | |
| NEOBEE microcapsules only | 0.81 |
| Ethyl Vanillin only | 1.31 |
| Ethyl vanillin/NEOBEE microcapsule pre-mix | 2.31 |
| Ethyl Vanillin and NEOBEE microcapsules (separately) | 1.34 |
| Heat dry Pre-Rub | |
| NEOBEE microcapsules only | 1.38 |
| Ethyl Vanillin only | 1.53 |
| Ethyl vanillin/NEOBEE microcapsule pre-mix | 2.50 |
| Ethyl Vanillin and NEOBEE microcapsules (separately) | 1.50 |
| Heat Dry Post-Rub | |
| NEOBEE microcapsules only | 1.31 |
| Ethyl Vanillin only | 1.66 |
| Ethyl vanillin/NEOBEE microcapsule pre-mix | 3.69 |
| Ethyl Vanillin and NEOBEE microcapsules (separately) | 1.59 |
| Line dry Pre-Rub | |
| NEOBEE microcapsules only | 1.31 |
| Ethyl Vanillin only | 1.18 |
| Ethyl vanillin/NEOBEE microcapsule pre-mix | 2.59 |
| Ethyl Vanillin and NEOBEE microcapsules (separately) | 1.19 |
| Line dry Post-Rub | |
| NEOBEE microcapsules only | 1.19 |
| Ethyl Vanillin only | 1.06 |
| Ethyl vanillin/NEOBEE microcapsule pre-mix | 4.19 |
| Ethyl Vanillin and NEOBEE microcapsules (separately) | 1.50 |
| Bloom During Ironing | |
| NEOBEE microcapsules only | 2.00 |
| Ethyl Vanillin only | 1.88 |
| Ethyl vanillin/NEOBEE microcapsule pre-mix | 3.00 |
| Ethyl Vanillin and NEOBEE microcapsules (separately) | 1.55 |

At all stages the Ethyl vanillin/NEOBEE microcapsule pre-mix significantly outperformed all other samples, in particular compared with the ethyl vanillin and NEOBEE microcapsules added separately to the base.

Example 5: Performance of Ethyl Vanillin Plus Microcapsule Premix in a Shampoo

Four samples were prepared in a shampoo base: Microcapsules (1.43% by weight) containing NEOBEE in the core (Sample 1); ethyl vanillin solution only (0.07% by weight) (Sample 2); a premix of ethyl vanillin plus pre-formed microcapsule with NEOBEE in the core (1.5% by weight) (Sample 3); and microcapsules (1.43% by weight)+ethyl vanillin solution (0.07% by weight) added separately to the shampoo (Sample 4). Each sample was used to wash and evaluate hair swatches. Each sample was evaluated at dry (pre- and post-brushing) using the LMS scale from 0-30, with 0 being the lowest and 30 being the highest on strength intensity. The results of this analysis are presented in Table 3.

TABLE 3

| Sample | Description | Mean Intensity | |
|---|---|---|---|
| | | Pre-Brush | Post-Brush |
| 1 | NEOBEE Microcapsules Only | 2.98 | 4.00 |
| 2 | Ethyl Vanillin Only | 3.87 | 4.32 |
| 3 | Ethyl Vanillin/NEOBEE microcapsule pre-mix | 4.61 | 11.91 |
| 4 | Ethyl Vanillin and NEOBEE microcapsules (separately) | 3.74 | 4.37 |

The ethyl vanillin/NEOBEE microcapsule pre-mix showed a significant benefit in strength at the post-brushing stage vs. all other samples. This analysis indicated that when the capsules and ethyl vanillin were premixed for a minimum of 24 hours, an interaction occurs which allow for the ethyl vanillin to be deposited in wash off products better than if it were added separately to a product.

Example 6: Performance of Ethyl Vanillin Plus Microcapsule Premix in a Shower Gel Two samples were prepared in shower gel: a premix of ethyl vanillin plus pre-formed microcapsule with NEOBEE in the core (4.77% by weight) (Sample 1); and microcapsules (4.52% by weight)+ethyl vanillin solution (0.24% by weight) added separately to the shower gel (Sample 2). The samples were applied to the forearms of the panelists in a randomized manner with one arm having Sample 1 and the other having Sample 2. Each arm was evaluated 5 hours after the application for pre- and post-rub using a scale from 0-10, with 0 being the lowest and 10 being the highest on strength intensity. The results of this analysis are presented in Table 4.

TABLE 4

| Sample | Description | Mean Intensity | |
|---|---|---|---|
| | | Pre-Rub | Post-Rub |
| 1 | Ethyl vanillin/NEOBEE microcapsule pre-mix | 2.90 | 5.50 |
| 2 | Ethyl Vanillin and NEOBEE microcapsules (separately) | 2.60 | 2.80 |

At the post-rub stage, ethyl vanillin/NEOBEE microcapsule pre-mix significantly outperformed the ethyl vanillin and NEOBEE microcapsules added separately to the base.

Example 7: Analytical Data of Ethyl Vanillin/Microcapsule Interaction

A 1% mixture of ethyl vanillin plus NEOBEE microcapsules were prepared. UV/VIS analysis was used to measure the initial concentration of the ethyl vanillin in the ethyl vanillin/NEOBEE microcapsule pre-mix at time 0. The slurry was aged for 3 and 4 weeks at room temperature and UV/VIS analysis was subsequently carried out to detect the presence of free ethyl vanillin in the premix over time. These measurements showed that the level of free ethyl vanillin decreased over that time period (Table 5).

TABLE 5

| Time of Aging | % ethyl vanillin |
|---|---|
| Time 0 | 1.1 |
| 3 Weeks | 0.19 |
| 4 Weeks | 0.16 |

Not wishing to be bound by theory, this analysis suggested that the ethyl vanillin is either migrating into the capsules or is attached to the outside of the wall.

Example 8: Tumble Dryer Sheet

A tumble dryer sheet was prepared using an ethyl vanillin capsule composition of this invention. The capsule composition contained 10% ethyl vanillin, and 48% of a model fragrance. The ratio of the neat fragrance to the pre-formed capsule was 6:2.2 by weight. The fragrance loaded onto a dryer sheet was 1.5 g.

The tumble dryer sheet was prepared by coating a melted tumble dryer coat mix (at 70° C.) and the ethyl vanillin composition onto a blank dryer sheet. After cooling to 25° C., Tumble Dryer Sheet 1 of this invention was obtained.

A comparable tumble dryer sheet was prepared the same way described above except that the neat fragrance was used without the pre-formed capsule.

Example 9: Evaluation of Tumble Dryer Sheet

Tumble Dryer Sheet 1 was evaluated by an expert panel for its fragrance performance with a scale of 0-100. A score of 5 indicates a weak fragrance intensity. A score of 18 indicates a moderate fragrance intensity. Fourteen towels were dried with one piece of the tumble dryer sheet for 30 minutes in a standard dryer. The fragrance intensity was evaluated right after the dryer door was opened. Tumble Dryer Sheet 1 had a fragrance intensity of 11.6. By contrast, the comparative tumble dryer sheet had a fragrance intensity of 10.7.

What is claimed is:

1. A fabric conditioner composition prepared by a method comprising the steps of:
   (a) mixing ethyl vanillin or vanillin with a slurry containing preformed friable shell-core microcapsules, each of which has a core and a shell, wherein the slurry comprises a solvent having a $Clog_{10}P$ that is greater than 3.3;
   (b) aging the mixture of step (a) for at least 24 hours to allow ethyl vanillin or vanillin to interact with the preformed friable shell-core microcapsules; and
   (c) combining the aged mixture of step (b) with the fabric conditioner composition,
   wherein the preformed friable shell-core microcapsules each have a diameter of 0.5 microns to 100 microns, and the ethyl vanillin or vanillin is added at a concentration of 0.05% to 20% by weight of the mixture of step (a).

2. The fabric conditioner composition of claim 1, wherein the friable shell-core microcapsules comprise a shell formed of urea-formaldehyde, melamine-formaldehyde, phenol-formaldehyde, or amido-aldehyde.

3. The fabric conditioner composition of claim 1, wherein the core contains a solvent.

4. The fabric conditioner composition of claim 1, further comprising a first fragrance in the slurry, a second fragrance in the core, or both.

5. The fabric conditioner composition of claim 4, wherein at least one of the first and second fragrances is a high performing fragrance.

6. The fabric conditioner composition of claim 1, wherein the fabric conditioner composition is a rinse aid composition.

7. The fabric conditioner composition of claim 1, wherein the fabric conditioner composition is a dryer sheet.

8. The fabric conditioner composition of claim 7, wherein the fabric conditioner composition is melted at an elevated temperature before it is combined with the aged mixture of step (b).

9. The fabric conditioner composition of claim 1, wherein the microcapsule composition of step (c) at a level of 0.05% to 5% by weight of conditioner composition.

10. The fabric conditioner composition of claim 1, wherein the preformed friable shell-core microcapsules each have a melamine formaldehyde shell and a diameter of 0.05 microns to 100 microns.

11. The fabric conditioner composition of claim 1, wherein the solvent has a $Clog_{10}P$ that is greater than 8.

12. The fabric conditioner composition of claim 1, wherein the solvent has a $Clog_{10}P$ that is greater than 10.

* * * * *